(12) United States Patent
Strohmer et al.

(10) Patent No.: US 9,347,590 B2
(45) Date of Patent: May 24, 2016

(54) COMPONENT FOR CONDUCTING OR RECEIVING A FLUID AND METHOD FOR TESTING THE COMPONENT

(71) Applicant: AREVA NP GMBH, Erlangen (DE)

(72) Inventors: Franz Strohmer, Bamberg (DE); Jens Saalfrank, Langensendelbach (DE)

(73) Assignee: Areva GmbH, Erlangen (DE)

( * ) Notice: Subject to any disclaimer, the term of this patent is extended or adjusted under 35 U.S.C. 154(b) by 729 days.

(21) Appl. No.: 13/746,513

(22) Filed: Jan. 22, 2013

(65) Prior Publication Data

US 2013/0181728 A1    Jul. 18, 2013

Related U.S. Application Data

(63) Continuation of application No. PCT/EP2011/061234, filed on Jul. 4, 2011.

(30) Foreign Application Priority Data

Jul. 21, 2010    (DE) .......................... 10 2010 031 610

(51) Int. Cl.
*G01N 27/02* (2006.01)
*F16L 11/127* (2006.01)
*F16L 9/12* (2006.01)
(Continued)

(52) U.S. Cl.
CPC ............... *F16L 11/127* (2013.01); *F16L 9/125* (2013.01); *F16L 57/06* (2013.01); *G01M 3/18* (2013.01); *G01M 3/186* (2013.01); *G01N 27/20* (2013.01); *B65D 90/508* (2013.01); *F16L 2201/30* (2013.01); *G21D 1/00* (2013.01)

(58) Field of Classification Search
None
See application file for complete search history.

(56) References Cited

U.S. PATENT DOCUMENTS 4,110,739 A     8/1978 Kidd
4,338,097 A *   7/1982 Turner et al. ...................... 436/6
(Continued)

FOREIGN PATENT DOCUMENTS

CN    101205999 A    6/2008
CN    100491809 C    5/2009
(Continued)

OTHER PUBLICATIONS

International Search Report of PCT/EP2011/061234.

*Primary Examiner* — Melissa Koval
*Assistant Examiner* — Courtney McDonnough
(74) *Attorney, Agent, or Firm* — Laurence A. Greenberg; Werner H. Stemer; Ralph E. Locher

(57) ABSTRACT

A component for conducting or receiving a fluid, in particular a component of a fluid-conducting line system of an industrial plant, especially of a line system of a tertiary cooling circuit of a nuclear power plant, includes a wall having a supporting structure made of a glass-fiber-reinforced plastic. Electrically insulating inner and outer protective layers are disposed on respective inner and outer surfaces of the supporting structure. An electrically conductive inner intermediate layer lies between the inner protective layer and the supporting structure and is provided with an electrical terminal. An electrically conductive outer intermediate layer lies between the outer protective layer and the supporting structure, is provided with an electrical terminal and is electrically insulated from the inner intermediate layer. A method for testing the component is also provided.

5 Claims, 1 Drawing Sheet

(51) Int. Cl.
*F16L 57/06* (2006.01)
*G01M 3/18* (2006.01)
*G01N 27/20* (2006.01)
*B65D 90/50* (2006.01)
*G21D 1/00* (2006.01)

(56) References Cited

U.S. PATENT DOCUMENTS

| | | | |
|---|---|---|---|
| 5,084,679 A * | 1/1992 | Lofgren | G01N 27/048 174/11 R |
| 5,214,387 A | 5/1993 | Fenner | |
| 5,228,478 A * | 7/1993 | Kleisle | 138/104 |
| 5,378,991 A | 1/1995 | Anderson et al. | |
| 5,388,991 A * | 2/1995 | Morris | 434/55 |
| 5,414,743 A * | 5/1995 | Batheja et al. | 376/299 |
| 2006/0091887 A1* | 5/2006 | Aisenbrey | 324/323 |
| 2010/0147409 A1 | 6/2010 | Lu et al. | |

FOREIGN PATENT DOCUMENTS

| | | |
|---|---|---|
| DE | 41 37 108 A1 | 5/1992 |
| GB | 2 287 817 A | 9/1995 |
| JP | S5788050 U | 5/1982 |
| JP | S61173045 U | 10/1986 |
| JP | H02259543 A | 10/1990 |

* cited by examiner

COMPONENT FOR CONDUCTING OR RECEIVING A FLUID AND METHOD FOR TESTING THE COMPONENT

CROSS-REFERENCE TO RELATED APPLICATION

This is a continuation, under 35 U.S.C. §120, of copending International Application No. PCT/EP2011/061234, filed Jul. 4, 2011, which designated the United States; this application also claims the priority, under 35 U.S.C. §119, of German Patent Application DE 10 2010 031 610.5, filed Jul. 21, 2010; the prior applications are herewith incorporated by reference in their entirety.

BACKGROUND OF THE INVENTION

Field of the Invention

The invention relates to a component for conducting or receiving a fluid, in particular a component of a fluid-conducting line system of an industrial plant, especially a line system of a tertiary cooling circuit of a nuclear power station. The invention relates, moreover, to a method for testing such a component.

The components of a fluid-conducting line system in industrial plants, for example in plants in the chemical industry or in power plants, for example the cooling lines in the tertiary cooling circuit of a nuclear power station, are often composed of underground, internally and externally rubberized steel lines or concrete pipes. Both types of pipe, however, are subject to wear due to corrosion or erosion and often have to be replaced in older nuclear power plants. Particularly in the case of nuclear power plants cooled by seawater, the corrosion of a steel line presents a serious problem, as soon as the rubberizing layer is attacked or damaged. For that reason, the components of those line systems which are composed of steel or concrete are replaced by components having a load-bearing structural element which is constructed from a glass fiber reinforced plastic, for example a composite material composed of glass fibers and epoxy resin (EP). The respective components are additionally provided both on their inside and their outside with a protective or reinforcing layer. The disadvantage of components of that type, however, is their restricted testability since commonly acceptable methods, such as for example, eddy-current testing, cannot be adopted, since they presuppose an electrically conductive material. Ultrasonic testing methods, although fundamentally possible, are nevertheless unsuitable for practical use because of the complex composite construction. At the present time, therefore, the testing of such components, which are constructed from a composite glass fiber/plastic material and which may not only be components of a line system, but also containers fillable with a fluid, is only carried out by a visual inspection, in such a way that a manipulator is inserted into the component to be tested and the inner surface of the latter is inspected with a video camera. Visual inspection is difficult, however, since the emptied components are usually wet and there are sometimes deposits, sludge and biofilm on the inner walls. Only conspicuous changes on the inner pipe wall can therefore be established by a visual inspection.

SUMMARY OF THE INVENTION

It is accordingly an object of the invention to provide a component for conducting or receiving a fluid and a method for testing the component, which overcome the hereinaforementioned disadvantages of the heretofore-known components and methods of this general type and in which the component is constructed on the basis of a glass fiber reinforced plastic and can be tested in a simple way for the presence of damage.

With the foregoing and other objects in view there is provided, in accordance with the invention, a component for conducting or receiving a fluid, in particular a component of a fluid-conducting line system of an industrial plant, especially of a line system of a tertiary cooling circuit of a nuclear power station. The component has a wall comprising a carrying structure composed of a glass fiber reinforced plastic, the carrying structure having inner and outer surfaces, electrically insulating inner and outer protective layers each disposed on a respective one of the inner and outer surfaces of the carrying structure, an electrically conductive inner intermediate layer having an electrical terminal and being disposed between the inner protective layer and the carrying structure, and an electrically conductive outer intermediate layer having an electrical terminal, being insulated electrically from the inner intermediate layer and being disposed between the outer protective layer and the carrying structure.

In this context, both pipelines and components of a fluid-conducting line system and stationary and transportable containers fillable with a fluid, that is to say receiving a fluid, are to be understood as being a component in the sense of the present invention.

By virtue of these measures, leakages in the carrying structure can be detected in a simple way by measurement of the electrical resistance between the inner and outer intermediate layers if the fluid located in the component is intrinsically electrically conductive or has been made electrically conductive at the measurement time by the addition of suitable chemical substances.

In accordance with another feature of the invention, since the production of the carrying structure takes place, as a rule, in a so-called winding method in which resin-impregnated glass fiber rovings are wound crosswise onto a rotating steel core, the production of the component is simplified if the intermediate layer or intermediate layers is or are formed by an electrically conductive fabric, since it can be applied in the same winding or application technique as the carrying structure.

With the objects of the invention in view, there is concomitantly provided a method for testing a component. The method comprises providing a component according to the invention and detecting an electrical resistance between the outer and inner intermediate layers. Thus, defects in the carrying structure can be detected by carrying out a simple electrical continuity test, that is to say by measuring the electrical resistance between the outer and inner intermediate layers if the fluid is electrically conductive.

Other features which are considered as characteristic for the invention are set forth in the appended claims.

Although the invention is illustrated and described herein as embodied in a component for conducting or receiving a fluid and a method for testing the component, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
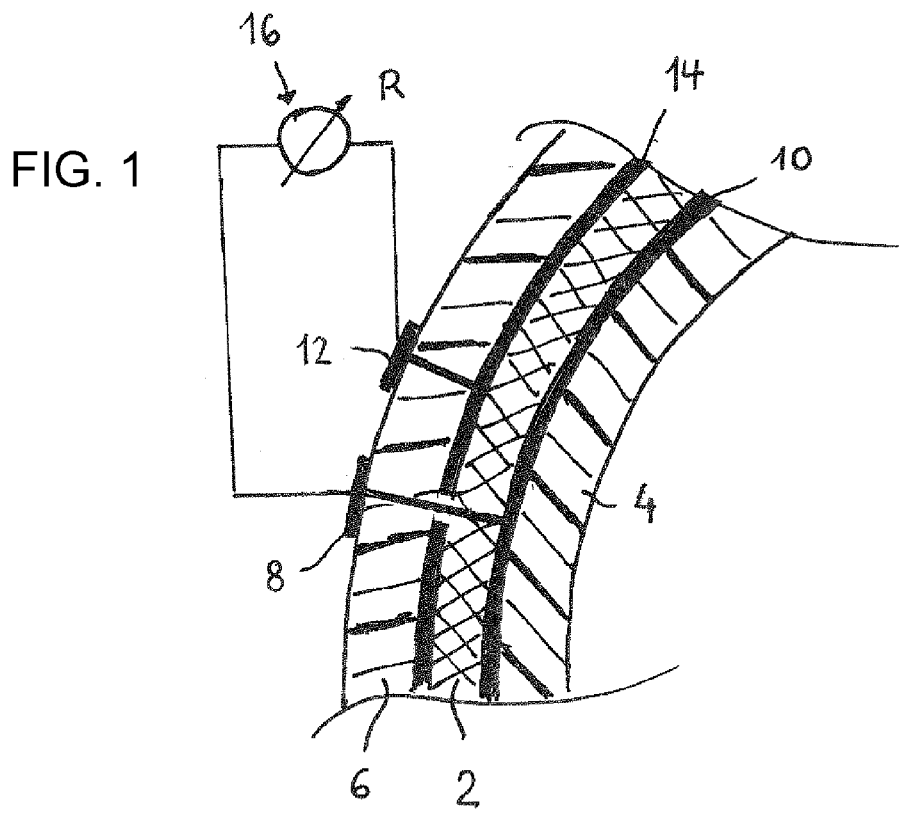
FIG. 1 is a fragmentary, diagrammatic, cross-sectional view of a wall of a component and a schematic view of a measuring device, according to the invention.

Referring now to the figures of the drawings in detail and first, particularly, to FIG. 1 thereof, there is seen a wall of a component of a fluid-conducting line system which is constructed from a carrying structure 2 serving as a load-bearing wall part. The carrying structure 2 is electrically nonconductive and is composed of a glass fiber reinforced composite material. The wall is provided on its inner surface and outer surface with respective electrically insulating inner and outer protective layers 4 and 6. An electrically conductive inner intermediate layer 10 provided with an electrical terminal 8 is located between the inner protective layer 4 and the carrying structure 2, and a likewise electrically conductive outer intermediate layer 14 provided with an electrical terminal 12 and insulated electrically from the inner intermediate layer 10 by the carrying structure 2 is located between the outer protective layer 6 and the carrying structure 2. In other words: the carrying structure 2 is provided on each of its inner and outer surfaces with a respective electrically conductive inner and outer intermediate layer 10 and 14, to which the inner and outer protective layers 4 and 6 are applied. The inner and outer protective layers 4 and 6 respectively protect the component against damage from the inside and outside. Line components in which abrasive particles, for example sand, are entrained by the coolant, are usually provided with an inner protective layer 4 made from rubber which is about 2 mm thick.

The electrical terminals 8 and 12 of the inner and outer electrically conductive intermediate layers 10 and 14 are accessible from outside and, for example, are disposed on the outside of the outer protective layer 6.

The electrically conductive intermediate layers 10 and 14 are manufactured from a netting or fabric, for example a fine silver netting, a high-grade steel fabric, a glass fiber netting or a glass fiber fabric with woven-in metal filaments or a carbon fiber composite material.

An electrical resistance R between the inner and outer intermediate layers 10 and 14 can be monitored by a measuring device 16. In the event of a leakage in the carrying structure 2 and in the inner protective layer 4, the fluid located inside the component penetrates into the carrying structure 2 and forces its way through it as far as the outer intermediate layer 14. If the fluid, usually water, located inside the component is electrically conductive, the electrical insulation properties of the carrying structure 2 are impaired correspondingly and the ohmic resistance R between the inner and outer intermediate layers 10 and 14 is reduced. Electrically nonconductive fluids may be made conductive for a measurement duration by an admixing of additives. Simple and reliable monitoring of the component for the occurrence of a leak is thereby possible.

Figure 2:
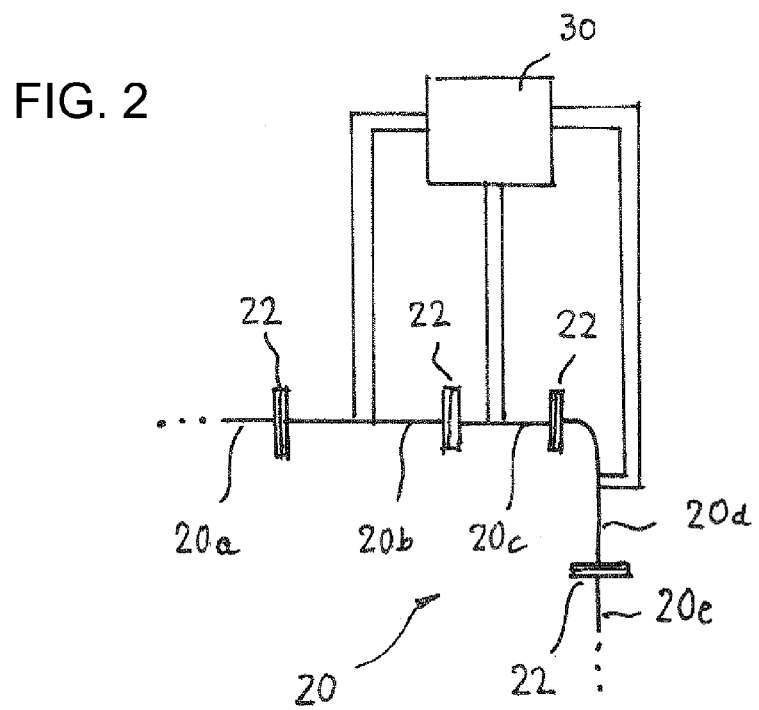
FIG. 2 is a basic schematic and diagrammatic view of a monitoring device of a line system assembled from a plurality of components to be monitored.

According to FIG. 2, a line system 20 is constructed from a plurality of components 20a-e and has pipeline parts connected to one another through flanges 22, as illustrated in the figure. Ohmic resistances between conductive intermediate layers of the individual components 20a-e are detected in a central monitoring device 30 which is provided for monitoring the line system 20. Thus, the occurrence of a leakage in the line system can be detected automatically and the component affected can be recognized.

The invention claimed is:

1. A component for conducting or receiving a fluid, the component comprising:
    a wall including:
        a carrying structure composed of a glass fiber reinforced plastic, said carrying structure having inner and outer surfaces;
        electrically insulating inner and outer protective layers each disposed on a respective one of said inner and outer surfaces of said carrying structure;
        an electrically conductive inner intermediate layer having an electrical terminal and being disposed between said inner protective layer and said carrying structure; and
        an electrically conductive outer intermediate layer having an electrical terminal, being insulated electrically from said inner intermediate layer and being disposed between said outer protective layer and said carrying structure;
    means for admixing an additive for a measurement duration to increase a conductivity of the fluid conducted or received by the component during a measurement process; and
    means for detecting an electrical resistance between the outer and inner intermediate layers.

2. The component according to claim 1, wherein said intermediate layers are formed by an electrically conductive fabric.

3. The component according to claim 1, wherein the wall is part of a component of a fluid-conducting line system of an industrial plant.

4. The component according to claim 1, wherein the wall is part of a component of a line system of a tertiary cooling circuit of a nuclear power station.

5. A method for testing a component, the method comprising the following steps:
    providing a component for conducting or receiving a fluid, the component having a wall including:
        a carrying structure composed of a glass fiber reinforced plastic, the carrying structure having inner and outer surfaces;
        electrically insulating inner and outer protective layers each disposed on a respective one of the inner and outer surfaces of the carrying structure;
        an electrically conductive inner intermediate layer having an electrical terminal and being disposed between the inner protective layer and the carrying structure; and
        an electrically conductive outer intermediate layer having an electrical terminal, being insulated electrically from the inner intermediate layer and being disposed between the outer protective layer and the carrying structure;
    admixing an additive for a measurement duration to increase a conductivity of the fluid conducted or received by the component during a measurement process; and
    detecting an electrical resistance between the outer and inner intermediate layers.

* * * * *